United States Patent
Hegel (10) Patent No.: US 8,425,589 B2
(45) Date of Patent: Apr. 23, 2013

(54) MECHANICAL LOCKING OF AN X-RAY MARKER IN THE EYELET OF A STENT OR IN ANOTHER BODILY IMPLANT

(75) Inventor: Alexander Hegel, Karlsruhe (DE)

(73) Assignee: Admedes Schuessler GmbH, Pforzheim (DE)

( * ) Notice: Subject to any disclaimer, the term of this patent is extended or adjusted under 35 U.S.C. 154(b) by 1413 days.

(21) Appl. No.: 11/412,689

(22) Filed: Apr. 26, 2006

(65) Prior Publication Data

US 2006/0259129 A1    Nov. 16, 2006

(30) Foreign Application Priority Data

Apr. 27, 2005  (DE) .......................... 10 2005 019 612

(51) Int. Cl.
*A61F 2/06* (2006.01)
(52) U.S. Cl.
USPC ........................................................ 623/1.34
(58) Field of Classification Search ................. 623/1.11, 623/1.15, 1.34; 606/191, 198
See application file for complete search history.

(56) References Cited

U.S. PATENT DOCUMENTS

| | | | |
|---|---|---|---|
| 5,443,500 A | 8/1995 | Sigwart | |
| 5,632,771 A | 5/1997 | Boatman et al. | |
| 5,741,327 A | 4/1998 | Frantzen | |
| 5,824,054 A | 10/1998 | Khosravi et al. | |
| 5,861,027 A | 1/1999 | Trapp | |
| 6,022,374 A | 2/2000 | Imran | |
| 6,231,598 B1 | 5/2001 | Berry et al. | |
| 6,293,966 B1 | 9/2001 | Frantzen | |
| 6,334,871 B1 | 1/2002 | Dor et al. | |
| 6,402,777 B1 | 6/2002 | Globerman et al. | |
| 6,409,752 B1 | 6/2002 | Boatman et al. | |
| 6,464,720 B2 | 10/2002 | Boatman et al. | |
| 6,730,116 B1 | 5/2004 | Wolinsky et al. | |
| 6,863,685 B2 | 3/2005 | Davila et al. | |
| 6,918,928 B2 | 7/2005 | Wolinsky et al. | |
| 2002/0193867 A1 | 12/2002 | Gladdish et al. | |
| 2002/0193869 A1 | 12/2002 | Dang | |
| 2003/0060872 A1 | 3/2003 | Gomringer et al. | |
| 2003/0106218 A1 | 6/2003 | Jalisi et al. | |
| 2003/0114912 A1 | 6/2003 | Sequin et al. | |
| 2004/0088038 A1 | 5/2004 | Dehnad et al. | |
| 2004/0088039 A1 | 5/2004 | Lee et al. | |
| 2004/0236407 A1 | 11/2004 | Fierens et al. | |

(Continued)

FOREIGN PATENT DOCUMENTS

| DE | 100 64 596 A1 | 12/2000 |
|---|---|---|
| DE | 102 35 868 A1 | 7/2002 |

(Continued)

OTHER PUBLICATIONS

Schumacher, M., "Diagnostic Workup in Cerebral Aneurysms," *Cerebral Aneurysms*, pp. 13-24, Nakstadt PHj (ed), Bologna, Centauro (2000).

*Primary Examiner* — Thomas J Sweet
*Assistant Examiner* — Matthew Schall
(74) *Attorney, Agent, or Firm* — Kilpatrick Townsend & Stockton LLP (57) ABSTRACT

A bodily implant, in particular a stent, for insertion or implantation into a living body, having a marker element made of an X-ray visible material which is inserted into a cutout in an implant structure is disclosed. The cutout has expansions on both of its opening sides, and the marker element is pressed or riveted into the cutout so that a positive fit is formed between the marker element and the implant structure.

13 Claims, 7 Drawing Sheets

U.S. PATENT DOCUMENTS

| | | |
|---|---|---|
| 2005/0060025 A1 | 3/2005 | Mackiewicz et al. |
| 2005/0172471 A1 | 8/2005 | Vietmeier |
| 2005/0256564 A1 | 11/2005 | Yang et al. |
| 2006/0085059 A1 | 4/2006 | Ehrlinspiel et al. |
| 2006/0217799 A1 | 9/2006 | Mailander et al. |
| 2006/0259129 A1 | 11/2006 | Hegel |
| 2007/0027552 A1 | 2/2007 | Farnsworth et al. |
| 2007/0043429 A1 | 2/2007 | Hegel |

FOREIGN PATENT DOCUMENTS

| | | |
|---|---|---|
| DE | 103 23 475 A1 | 12/2004 |
| DE | 04 014 789 | 3/2005 |
| EP | 0 737 452 A1 | 10/1996 |
| EP | 0 800 800 A1 | 10/1997 |
| EP | 0 801 933 A1 | 10/1997 |
| EP | 0 938 879 A2 | 9/1999 |
| EP | 0 997 116 A2 | 5/2000 |
| EP | 0 891 166 B1 | 1/2005 |
| EP | 1 523 959 A2 | 4/2005 |
| WO | WO 95/01761 A2 | 1/1995 |
| WO | 98/31304 A1 | 7/1998 |
| WO | WO 99/02092 A1 | 1/1999 |
| WO | WO 99/15108 A2 | 4/1999 |
| WO | WO 02/24247 A1 | 3/2002 |
| WO | WO 03/101343 A1 | 12/2003 |
| WO | WO 2004/002368 A1 | 1/2004 |

Section C-C

MECHANICAL LOCKING OF AN X-RAY MARKER IN THE EYELET OF A STENT OR IN ANOTHER BODILY IMPLANT

CROSS-REFERENCES TO RELATED APPLICATIONS

The present invention claims priority to German Patent Application No. 10-2005-019612.8-43, filed on Apr. 27, 2005 which is incorporated by reference.

BACKGROUND OF THE INVENTION

The present invention relates to a bodily implant, in particular a stent, for insertion into a living body, having good X-ray visibility, and a method for manufacturing such a bodily implant, and a method for enabling or improving the X-ray visibility of a bodily implant.

Bodily implants or stents of this type protect channels in living bodies such as blood vessels, the esophagus, the urethra, or renal passages, by insertion of the stent and expansion of same inside the bodily channel. In this manner, collapse or occlusion of the particular bodily channel may be prevented. A stent is also used, for example, for intercerebral aneurysms, which are the most common cause of non-traumatic subarachnoid hemorrhages. The incidence of these hemorrhages is approximately 1% in the general population, and, according to autopsy studies, possibly as high as 9%. From a patho-morphological standpoint, intracerebral aneurysms as a rule are genuine saccular aneurysms which are usually localized in vascular arborizations (see, for example, Schumacher, M., "Diagnostic workup in cerebral aneurysms" in Nakstadt PHj (ed.): "Cerebral Aneurysms," pp. 13-24, Bologna: Centauro (2000)).

Such bodily implants or stents may also be used as carriers for medications to enable local therapy within the bodily channel. Stents are inserted in a collapsed state into a bodily channel, and are expanded after being positioned in the bodily channel. These stents are usually composed of stainless steel or a cobalt-chromium-tantalum alloy. The stents are preferably inserted into the bodily channel by means of an expansion device, such as a balloon catheter, for example, and are expanded there.

The stents may also be composed of other materials, for example polymers, self-degradable materials such as lactic acid materials or derivatives thereof, in addition to nitinol (nickel-titanium alloys) and/or other self-expanding materials such as so-called shape memory materials.

To increase the X-ray visibility of these stents, the stents are often provided with additional elements (known as markers) which are produced from a material having high X-ray visibility. A type of stent is disclosed in U.S. application Ser. No. 11/365,470, filed Feb. 28, 2006, which claims priority from German Application No. 10-2005-013547.1-43, filed Mar. 23, 2005, which are incorporated herein by reference for all purposes.

BRIEF SUMMARY OF THE INVENTION

The present invention is directed to providing a bodily implant having good X-ray visibility which is simple and economical to manufacture, a method for manufacturing such a bodily implant, and a method for enabling or improving the X-ray visibility of a bodily implant.

The bodily implant according to the invention, in particular a stent, for insertion or implantation into a living body has a marker element made of an X-ray visible material which is inserted into a cutout in an implant structure, the cutout having expansions on both of its opening sides so that a conical shape of an exterior side of the implant structure lies adjacent to a conical expansion of an interior side of the implant structure to form a double cone, the marker element being pressed or riveted into the cutout.

As a result of the cutout in the implant structure being outwardly expanded on both opening sides of the cutout, and the marker element being pressed or riveted into the cutout, the marker element makes a positive fit in the implant structure so that the marker element is securely fastened in the implant structure.

In some embodiments, the cutout has an essentially circular shape, and the expansions in each case are essentially conical, the cone angle of the expansions being in the range of approximately 5 degrees to approximately 120 degrees. In some embodiments, the cone angle is approximately 15 degrees to approximately 105 degrees. Because of the acute angle of the cutout, the essentially cylindrical rough marker element is slightly deformed to assume the shape of a double cone.

In addition, both the cutout and the cylindrical marker element may have a relatively large manufacturing tolerance, since these manufacturing tolerances may be compensated for by the riveting or pressing of the marker element into the cutout.

In some embodiments, the marker element is essentially cylindrical before being pressed in, and after pressing or riveting assumes the shape of a double cone, whereby after the pressing or riveting the marker element is essentially flush with the implant structure on the inside and outside.

By virtue of the marker element being essentially flush with the implant structure after being pressed in, it is possible to avoid transitional edges, which otherwise could cause injury to the bodily channel during insertion.

In some embodiments, the marker element comprises a material having good X-ray visibility, i.e., a material with high absorption of X-ray beams, for example gold, platinum, tantalum, platinum alloy, platinum-iridium, or niobium.

The present invention further relates to a method for increasing or enabling the X-ray visibility of a bodily implant, in particular a stent, comprising: forming a cutout in an implant structure by means of a laser so that the cutout assumes a conical shape on an exterior side of an implant structure; providing a conical expansion of an interior side of the implant structure so that the conical shape lies adjacent to the conical expansion to form a double cone; inserting an essentially cylindrical marker element into the cutout; and pressing the marker element. In some embodiments, the conical expansion is preferably applied on the interior side by drilling. The conical expansion is applied in essentially up to half the wall thickness of the bodily implant.

The present invention further relates to a method for manufacturing a bodily implant, in particular a stent, having an X-ray visible marker element, comprising: forming a cutout in an implant structure; expanding the cutout outwardly on both opening sides so that a conical shape on an exterior side of the implant structure lies adjacent to a conical expansion of an interior side of the implant structure to form a double cone; and pressing or riveting in the marker element. In some embodiments, the conical expansion is preferably applied on the interior side by drilling. The conical expansion is applied in essentially up to half the wall thickness of the bodily implant, resulting in high strength, i.e., mechanical locking, of the marker element in the cutout in the implant structure.

The following detailed description together with the accompanying drawings will provide a better understanding of the nature and advantages of the present invention.

DETAILED DESCRIPTION OF THE INVENTION

As shown in FIGS. 1 through 4, an implant structure 11 of a bodily implant 1 has a curved, circular, ellipsoidal, or cylindrical shape in order to lie flat against the walls of a bodily channel or cavity. A cutout 10 for insertion of a marker element 2 (FIG. 5) is formed by laser cutting of the implant structure 11. As a result of the laser cutting and the curved shape of the implant structure 11, at least in places, the cutout 10 for insertion of the marker element 2 assumes a conical shape (angle a), shown most clearly in FIG. 2. To form a double cone, an inner cone 14 (angle β) is formed in the cutout 10, from an interior side toward the outside, such that both the outer cone 12 and the inner cone 14 extend inwardly. The outer and inner cones 12, 14 may lie adjacent to one another or may be separated by a distance. When the cones lie adjacent to one another, a shape which approximates a double cone results, whereas when the outer cone 12 is separated by a distance from the inner cone 14 (not shown), an approximately cylindrical section results between the outer and inner cones 12, 14.

In the embodiment illustrated, the outer and inner cones 12, 14 lie adjacent to one another so as to form a ridge 13 at the intersection of the outer and inner cones 12, 14. As shown in FIGS. 1 through 4, the ridge 13 extends around a majority of the cutout 10.

A marker element 2 may be inserted into this double cone by pressing or riveting, thereby ensuring a positive fit of the marker element 2. This results in high mechanical strength, i.e., locking, of the marker element 2 in the bodily implant 1. Adhesive bonding, welding, etc. is thus unnecessary, thereby allowing the manufacturing costs for the bodily implant 1 to be kept low.

In some embodiments, the inner cone 14 is applied by drilling in the cutout 10 (so-called eyelet) of the bodily implant 1. However, both the inner cone 14 and the outer cone 12 may also be provided by laser cutting, etching, erosion, etc. It should be appreciated that the invention is not limited to the shape of a cone 12, 14. Instead, any other shape of an expansion 12, 14 may be applied in the cutout 10, provided that a positive fit or barbed hook effect is formed or produced between the marker element 2 and the cutout 10. Thus, the expansion may be applied, for example, only in certain peripheral regions of the cutout 10, such as four expansions, each offset from one another by 90° in the peripheral direction.

A continuous expansion or a convex expansion may also be applied instead of a cone 12, 14, as long as an interior surface of the cutout 10 is configured not radially (as for a cylinder) but instead is inclined at an angle with respect to the center axis of the cutout 10, to form a positive fit or barbed hook effect of a marker element 2 in the cutout 10. However, the double cone may also be used on flat structures, sheets, for example, if the outer cone 12 having the angle a is additionally applied. In some embodiments, the outer cone 12 is produced by laser cutting of the cutout 10 (eyelet) for a cylindrical bodily implant 1, such as a stent.

Figure 1:
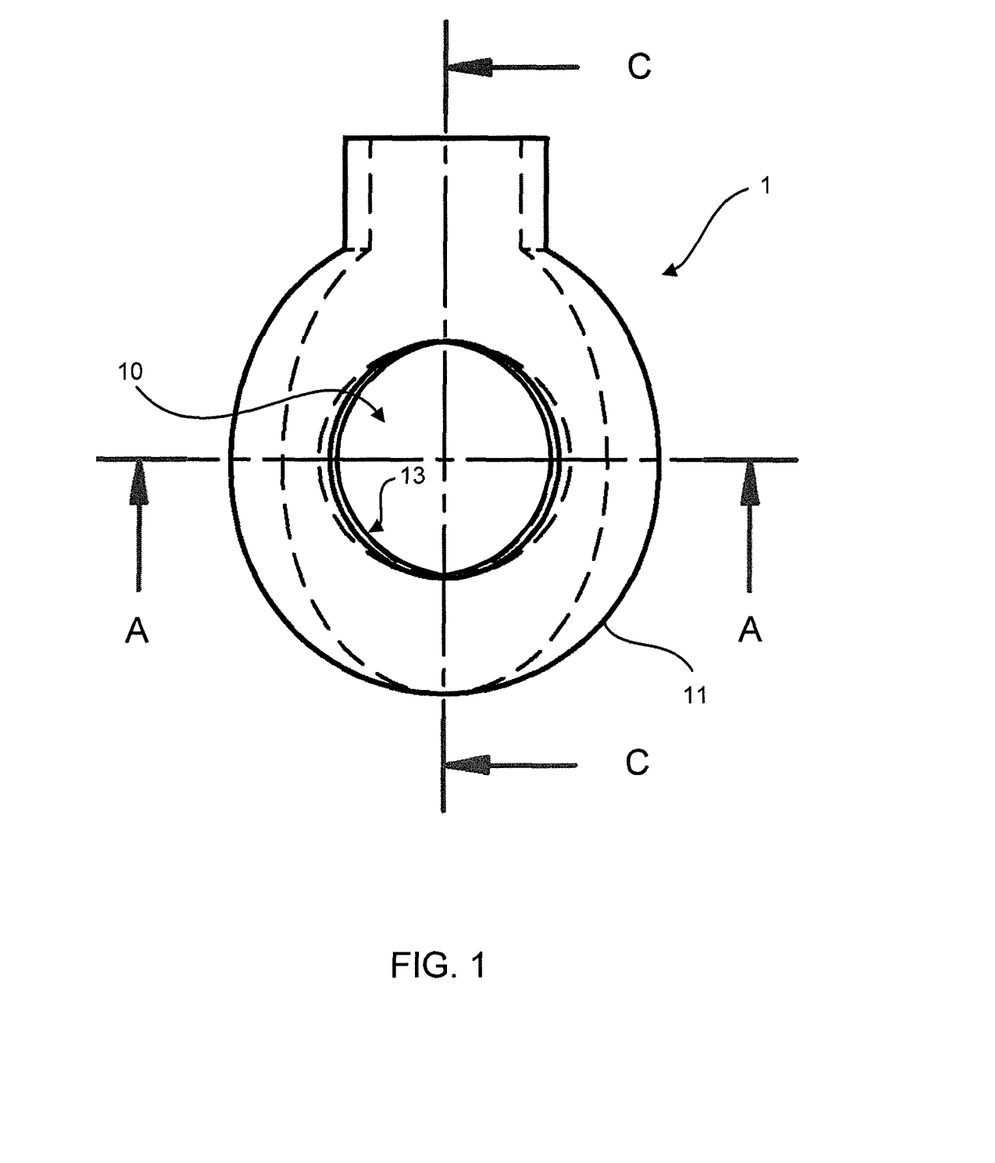
FIG. 1 shows a portion of an implant structure having a central cutout in accordance with an embodiment of the present invention.
Figure 2:
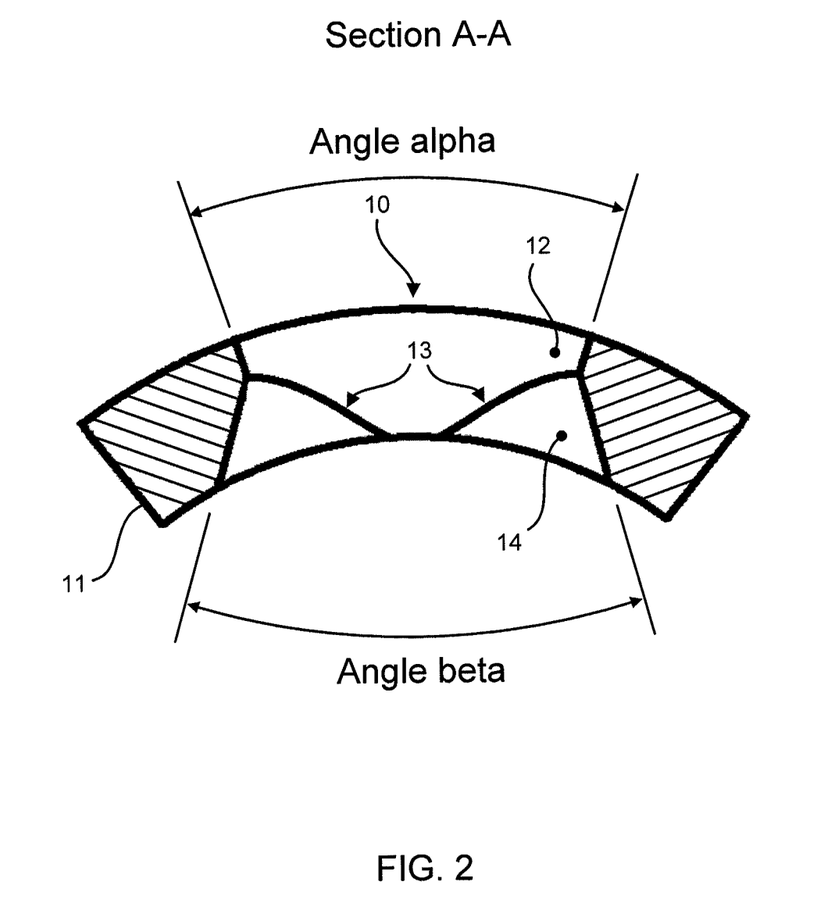
FIG. 2 shows the implant structure illustrated in FIG. 1, in the section A-A.
Figure 3:
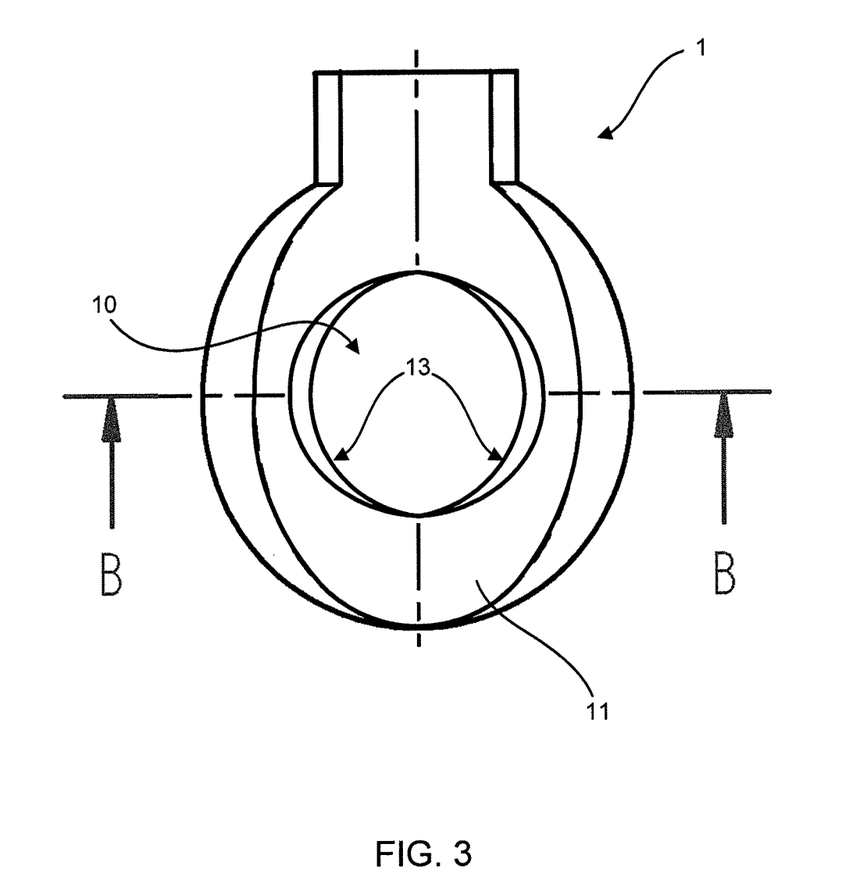
FIG. 3 shows the implant structure illustrated in FIG. 1, viewed from the underside.
Figure 4:
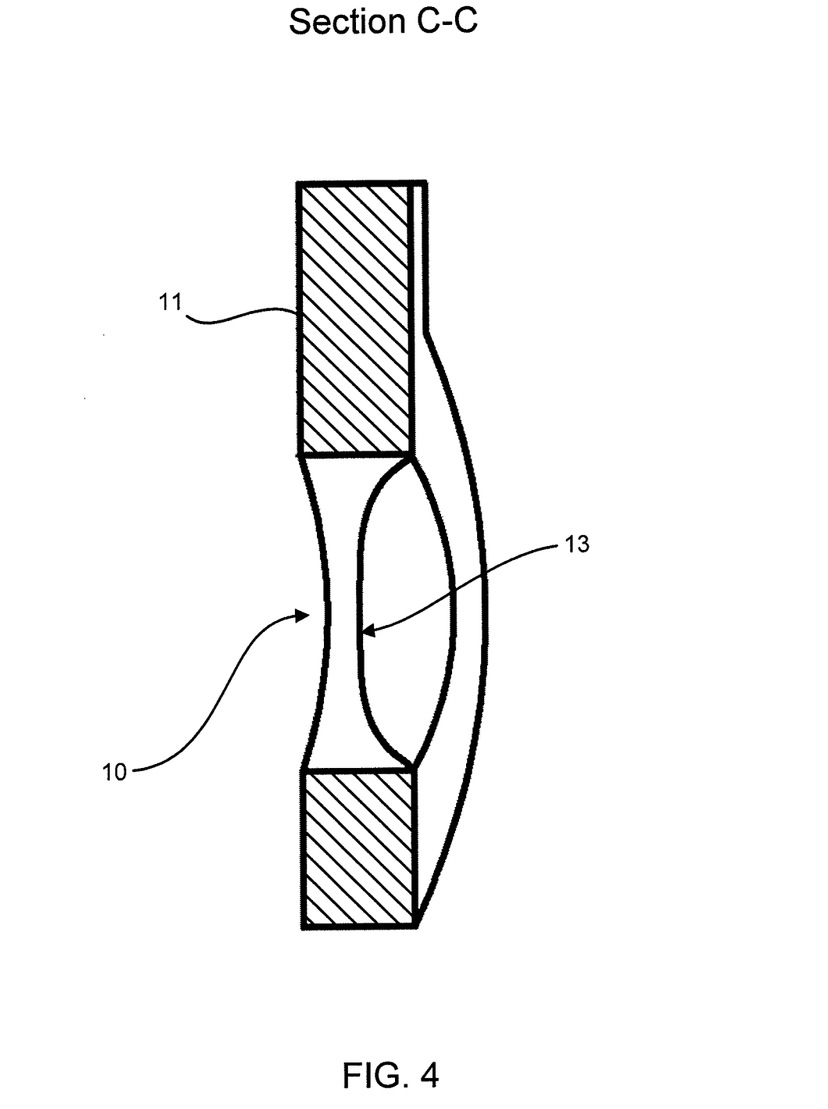
FIG. 4 shows the implant structure illustrated in FIG. 1, in the section C-C.
Figure 5:
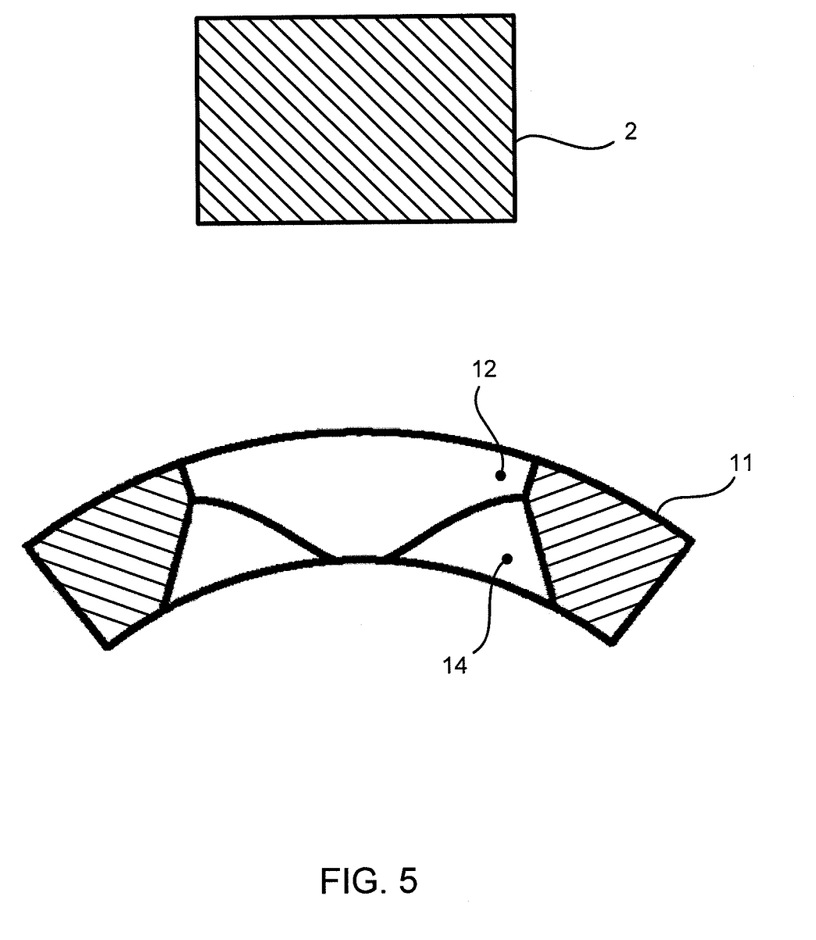
FIG. 5 shows the cylindrical marker element together with the implant structure before the marker element is inserted into the cutout in accordance with an embodiment of the present invention.
Figure 6:
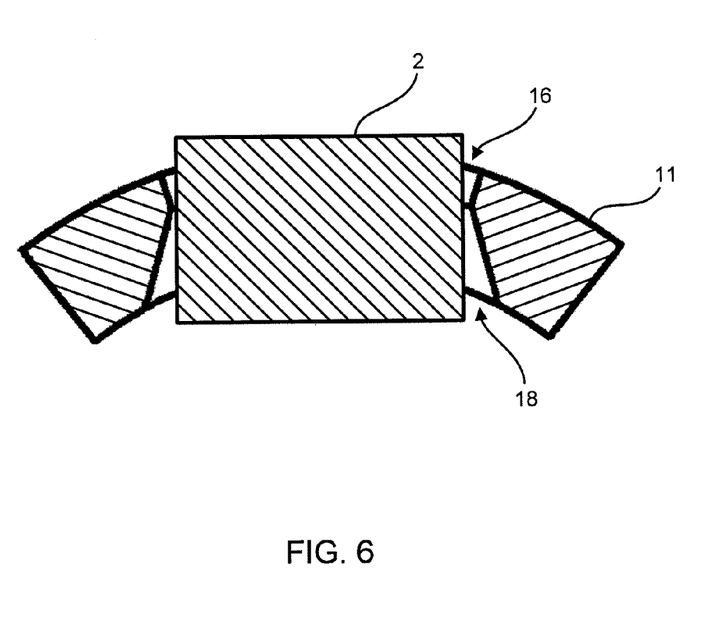
FIG. 6 shows the cylindrical marker element together with the implant structure after the marker element is inserted into the cutout in accordance with an embodiment of the present invention.
Figure 7:
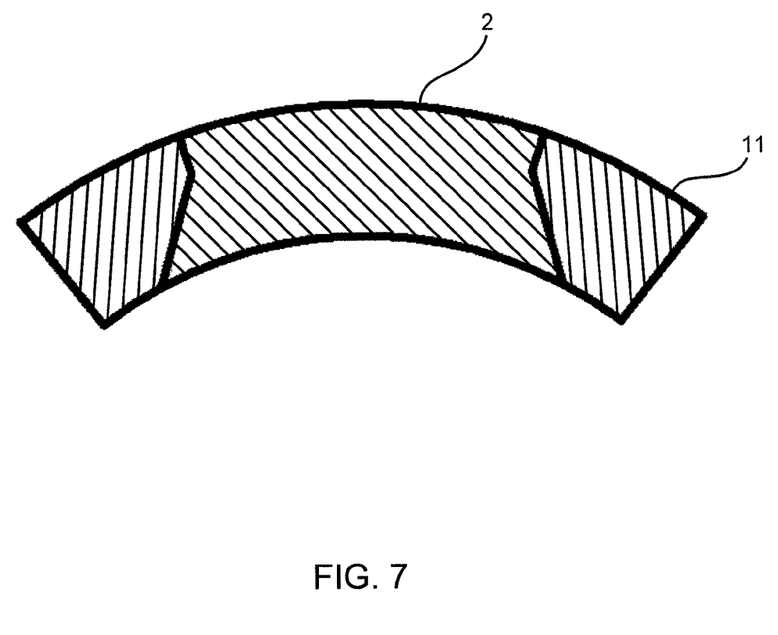
FIG. 7 shows the implant structure, together with the marker element inserted into the cutout, after the marker element has been pressed or riveted in accordance with an embodiment of the present invention.

FIGS. 5 through 7 show the steps for attaching the marker element 2 to the bodily implant 1. First, as shown in FIG. 5, the inner cone 14 is applied on the implant structure 11. Then, as shown in FIG. 6, the cylindrical marker element 2 is inserted into the cutout 10 so that the marker element 2 protrudes on both an interior side and an exterior side of the bodily implant 1. However, depending on the riveting tool used, the marker element 2 may also be inserted so that it does not protrude from the bodily implant 1, or protrudes from only one side. The cylindrical shape of the marker element 2 and the double-conical or conical shape of the cutout 10 result in an annular gap 16, 18 on both the exterior side and the interior side, respectively, of the bodily implant 1, between the marker element 2 and the implant structure. This annular gap 16, 18 accommodates the material of the marker element 2 during pressing or riveting of the marker element 2.

FIG. 7 shows the pressed marker element 2 in the bodily implant 1. In some embodiments, the marker element 2 preferably is pressed in such a way that it forms an essentially flat surface with the implant structure 11. Edges at the transition between the marker element 2 and the bodily implant 1, which otherwise could result in injury of a bodily channel in which the bodily implant 1 is inserted, are thereby avoided.

Because the material of the marker element 2 flows into the annular gap 18, the manufacturing tolerances for both the cutout 10 and the marker element 2 can be relatively high, since the caulking effect of the marker element material can compensate for these manufacturing tolerances.

In some embodiments, the marker 2 comprises an X-ray visible material, for example gold, platinum, tantalum, niobium, or a platinum alloy such as platinum-iridium. The dimensions of the marker element 2 may be matched to the cutout 10 such that, after pressing, the marker element 2 is essentially flush with the implant structure on the inside and outside. However, if there is an increased demand for flatness, the marker element 2 may also be dimensioned slightly larger, and after pressing may undergo surface treatment, for example by a laser, electropolishing, or grinding.

The expansions 12, 14 of the cutout 10 form a positive fit between the marker element 2 and the implant structure 11, thus ensuring a good attachment of the marker element 2 in the implant structure. Adhesive bonding or welding may be omitted to economize on production costs. However, adhesive bonding or welding may also be performed in addition to the positive fit.

In some embodiments, the bodily implant 1 comprises one of the following materials: stainless steel, cobalt-chromium-tantalum alloy, polymers, self-degradable materials such as lactic acid materials or derivatives thereof, in addition to nitinol (nickel-titanium alloys) and/or other self-expanding materials such as so-called shape memory materials.

While the present invention has been described with respect to specific embodiments, those skilled in the art will appreciate that the invention is intended to cover all modifications and equivalents within the scope of the following claims.

What is claimed is:

1. An apparatus for insertion or implantation into a living body comprising:
    a marker element made of an X-ray visible material which is inserted into a cutout in an implant structure, the cutout having expansions extending substantially continuously around the cutout on both of its opening sides so that a conical surface of an exterior side of the implant structure intersects a conical surface of an interior side of the implant structure to form a double cone, wherein the two conical surfaces form at least one ridge that extends around a majority of the cutout, wherein the marker element is pressed or riveted into the cutout.

2. The apparatus according to claim 1, wherein the cutout has an essentially circular shape, and the expansions are essentially conical.

3. The apparatus according to claim 2, wherein the cone angle $(\alpha, \beta)$ of the expansions is in the range of approximately 5 degrees to approximately 120 degrees.

4. The apparatus according to claim 3, wherein the marker element is essentially cylindrical before being pressed in, and after pressing or riveting has the shape of a double cone.

5. The apparatus according to claim 1, wherein after pressing or riveting the marker element, the marker element is essentially flush with the implant structure on the inside and outside.

6. The apparatus according to claim 1, wherein the marker element comprises gold, platinum, tantalum, platinum alloy, platinum-iridium, or niobium.

7. An apparatus for insertion or implantation into a living body comprising:
    an implantable structure comprising a cutout having one or more expansions on an exterior side of the cutout and one or more expansions on an interior side of the cutout, the one or more exterior-side expansions extending substantially continuously around the cutout, the one or more interior-side expansions extending substantially continuously around the cutout, wherein one or more of the exterior-side expansions intersect one or more of the interior-side expansions to form at least one ridge that extends around a majority of the cutout such that the cutout comprises a double cone shape; and
    a marker element made of an X-ray visible material and that is at least one of pressed or riveted into the cutout.

8. The apparatus according to claim 7, wherein:
the one or more exterior-side expansions comprise a plurality of expansions; and
the one or more interior-side expansions comprise a plurality of expansions.

9. The apparatus according to claim 7, wherein:
the cutout has an essentially circular shape;
each of the one or more exterior-side expansions are substantially conically shaped; and
each of the one or more interior-side expansions are substantially conically shaped.

10. The apparatus according to claim 9, wherein the cone angle $(\alpha, \beta)$ of each of the exterior-side and interior-side expansions is in the range of approximately 5 degrees to approximately 120 degrees.

11. The apparatus according to claim 10, wherein the marker element is essentially cylindrical before being pressed in, and after pressing or riveting has the shape of a double cone.

12. The apparatus according to claim 7, wherein after pressing or riveting the marker element, the marker element is essentially flush with the implant structure on the inside and outside.

13. The apparatus according to claim 7, wherein the marker element comprises gold, platinum, tantalum, platinum alloy, platinum-iridium, or niobium.

* * * * *